(12) United States Patent
Kadota et al.

(10) Patent No.: US 7,656,070 B2
(45) Date of Patent: Feb. 2, 2010

(54) SURFACE WAVE SENSOR APPARATUS

(75) Inventors: Michio Kadota, Kyoto (JP); Koji Fujimoto, Otsu (JP)

(73) Assignee: Murata Manufacturing Co., Ltd., Kyoto (JP)

( * ) Notice: Subject to any disclaimer, the term of this patent is extended or adjusted under 35 U.S.C. 154(b) by 0 days.

(21) Appl. No.: 11/843,527

(22) Filed: Aug. 22, 2007

(65) Prior Publication Data
US 2007/0284966 A1 Dec. 13, 2007

Related U.S. Application Data

(63) Continuation of application No. PCT/JP2005/006774, filed on Apr. 6, 2005.

(51) Int. Cl.
H03H 9/145 (2006.01)
(52) U.S. Cl. .................. 310/313 R; 310/363; 310/364; 310/365; 310/366
(58) Field of Classification Search ................. 310/313, 310/363, 364, 365, 366
See application file for complete search history.

(56) References Cited

U.S. PATENT DOCUMENTS

| | | | | |
|---|---|---|---|---|
| 5,216,312 A * | 6/1993 | Baer et al. | | 310/313 D |
| 5,910,286 A | 6/1999 | Lipskier | | |
| 6,543,274 B1 | 4/2003 | Herrmann et al. | | |
| 6,640,613 B2 | 11/2003 | Rapp et al. | | |
| 6,759,928 B2 | 7/2004 | Endou et al. | | |
| 6,815,830 B2 * | 11/2004 | Miyasaka | | 257/778 |
| 6,928,718 B2 * | 8/2005 | Carpenter | | 29/594 |
| 6,965,282 B2 | 11/2005 | Kawachi et al. | | |
| 7,019,435 B2 * | 3/2006 | Nakaya et al. | | 310/313 D |
| 2003/0122453 A1 * | 7/2003 | Yamada et al. | | 310/363 |
| 2004/0088842 A1 * | 5/2004 | Maruyama et al. | | 29/25.35 |
| 2004/0216534 A1 * | 11/2004 | Ruhrig et al. | | 73/862.626 |
| 2006/0053607 A1 * | 3/2006 | Onozawa | | 29/25.35 |
| 2007/0145862 A1 | 6/2007 | Kimura et al. | | |
| 2007/0154349 A1 | 7/2007 | Kimura et al. | | |

FOREIGN PATENT DOCUMENTS

| | | |
|---|---|---|
| JP | 63-250560 A | 10/1988 |
| JP | 05-045338 A | 2/1993 |

(Continued)

OTHER PUBLICATIONS

Official communication issued in the counterpart International Application No. PCT/JP2005/006774, mailed on Jul. 19, 2005.

(Continued)

*Primary Examiner*—Walter Benson
*Assistant Examiner*—Bryan P Gordon
(74) *Attorney, Agent, or Firm*—Keating & Bennett, LLP.

(57) ABSTRACT

A surface wave sensor apparatus has a structure such that, on a first principal surface of a base substrate having first through-hole conductors, surface acoustic wave devices are bonded via thermo-compression anisotropic conductive sheets, on first principal surfaces of piezoelectric substrates of the surface acoustic wave devices, electrodes, such as IDTs, are provided, respectively. These electrodes extend toward second principal surfaces via second through-hole conductors and are provided in the piezoelectric substrates. The first through-hole conductors overlap with the second through-hole conductors with the thermo-compression anisotropic conductive sheets being disposed therebetween, respectively.

18 Claims, 6 Drawing Sheets

FOREIGN PATENT DOCUMENTS

| | | |
|---|---|---|
| JP | 05-045339 A | 2/1993 |
| JP | 05-308163 A | 11/1993 |
| JP | 08-181563 A | 7/1996 |
| JP | 10041776 * | 7/1996 |
| JP | 09-512345 A | 12/1997 |
| JP | 10-41776 A | 2/1998 |
| JP | 10041776 * | 2/1998 |
| JP | 2001-102905 A | 4/2001 |
| JP | 2003-502616 A | 1/2003 |
| WO | 2006/027893 A1 | 3/2006 |
| WO | 2006/027945 A1 | 3/2006 |

OTHER PUBLICATIONS

Official communication issued in the counterpart Taiwanese Application No. 094139026, mailed on Aug. 29, 2007.

* cited by examiner

SURFACE WAVE SENSOR APPARATUS

BACKGROUND OF THE INVENTION

1. Field of the Invention

The present invention relates to surface wave sensor apparatuses capable of detecting a target detection substance by changes in mass loading, and in particular, the present invention relates to a surface wave sensor apparatus suitable for detecting a target detection substance in a liquid.

2. Description of the Related Art

Various sensors have been proposed for detecting a substance contained in liquid. For example, in Japanese Unexamined Patent Application Publication No. 2001-102905, an in-liquid substance detection sensor detecting a substance in liquid using surface acoustic waves is disclosed.

FIG. 9 is a schematic front sectional view illustrating the in-liquid substance detection sensor described in Japanese Unexamined Patent Application Publication No. 2001-102905.

In this drawing, an in-liquid substance detection sensor 102 is dipped into a solution 101 containing a target detection substance. The in-liquid substance detection sensor 102 includes a surface wave device. That is, the in-liquid substance detection sensor 102 includes a rectangular plate-shaped piezoelectric substrate 103, an input IDT electrode 104 spaced from one side of the piezoelectric substrate 103 by a predetermined distance, and an output IDT electrode 105. Between the input IDT electrode 104 and the output IDT electrode 105, a film 106 is provided for absorbing a target detection substance. When an AC voltage is applied across the input IDT electrode 104 herein, surface acoustic waves are generated in the piezoelectric substrate 103. The surface acoustic waves propagate toward the output IDT electrode 105. Then, from the output IDT electrode 105, an electric signal due to the propagated surface waves is derived. Since the film 106 absorbs the target detection substance, the existence of the target detection substance changes the load applied on the surface of the piezoelectric substrate 103. Accordingly, the propagated surface acoustic waves are changed, so that the output derived from the output IDT electrode 105 is varied due to the existence of the target detection substance, enabling the presence and the density of the target detection substance to be detected.

However, in the measuring method using the in-liquid substance detection sensor 102, the in-liquid substance detection sensor 102 must be dipped into a liquid 101. Hence, when a small amount of the liquid 101, which is a target object, is only prepared, there has been a problem that the substance contained in the liquid 101 cannot be detected.

Also, even when a large amount of the liquid 101 is prepared, if the liquid is expensive, a problem of high measuring cost may arise.

In addition, since the liquid 101 adheres to regions other than the region where the surface acoustic waves propagate, i.e., regions where electrode pads and bonding wires connected to the IDT electrodes 104 and 105 are arranged, there also has been a problem that electric characteristics are changed, so that detection accuracies are deteriorated in the in-liquid substance detection sensor 102.

On the other hand, in Japanese Unexamined Patent Application Publication No. H10-41776 and Japanese Unexamined Patent Application Publication No. 2001-102905, as shown in front sectional views of FIGS. 10 and 11, surface acoustic wave apparatuses are disclosed. The surface acoustic wave apparatuses described in Japanese Unexamined Patent Application Publication No. H10-41776 and Japanese Unexamined Patent Application Publication No. 2001-102905 define a resonator and a filter utilizing electric characteristics of a surface acoustic wave device, and are not used for substance detection.

As shown in FIG. 10, a surface wave apparatus 201 includes a base substrate 202 and a frame 203 fixed on the base substrate 202. The base substrate 202 and the frame 203 are made of ceramics such as alumina. Terminal electrodes 204 and 205 are arranged to extend from the top surface of the base substrate 202 to the bottom surface thereof. The terminal electrodes 204 and 205 lead to the region surrounded with the frame 203, and in the region surrounded with the frame 203, an anisotropic conductive sheet 206 is laminated on the terminal electrodes 204 and 205.

On the anisotropic conductive sheet 206, a surface acoustic wave device 207 is stacked and on the surface acoustic wave device 207, an elastic sheet 208 is laminated. Then, a lid 209 is fixed on the upper surface of the frame 203 so as to press the elastic sheet 208. Hence, the electrode on the bottom surface of the surface acoustic wave device 207 is to be securely connected, due to an elastic force of the elastic sheet 208, to the terminal electrodes 204 and 205 with the anisotropic conductive sheet 206 therebetween.

On the other hand, as shown in FIG. 11, in a surface acoustic wave apparatus 251 described in Japanese Unexamined Patent Application Publication No. 2001-102905, on the bottom surface of a base substrate 252, external electrodes 253 and 254 are formed. Through-hole conductors 255 and 256 are arranged to lead to the bottom surface of the base substrate 252 from the upper surface thereof so as to be electrically connected to the external electrodes 253 and 254, respectively. On the upper surface of the base substrate 252, terminal electrodes 257 and 258 are arranged so as to be electrically connected to the upper ends of the through-hole conductors 255 and 256, respectively. To the terminal electrodes 257 and 258, a surface acoustic wave device 259 is electrically connected with metallic bumps 260 and 261, respectively. In the surface acoustic wave device 259, through-hole conductors 263 and 264 are formed within a piezoelectric substrate 262. First ends of the through-hole conductors 263 and 264 are electrically connected to the metallic bumps 260 and 261, respectively. The upper ends of the through-hole conductors 263 and 264 are electrically connected to electrodes, such as an IDT 266, formed on the upper surface of the piezoelectric substrate 262, respectively.

In order to achieve the electrical connection by the bumps 260 and 261 and to bond the surface acoustic wave device 259 on the base substrate 252, a die-bonding member 267 herein is provided between the surface acoustic wave device 259 and the base substrate 252.

In the in-liquid substance detection sensor 102 described in Japanese Unexamined Patent Application Publication No. 2001-102905, as mentioned above, it must be dipped into the liquid 101 and when a small amount of the liquid 101 is only prepared, the substance contained in the liquid 101 cannot be detected. In addition, since the liquid 101 adheres to regions other than the region where the surface waves propagate, i.e., regions where electrode pads and bonding wires are arranged, there has been also a problem of insufficient detection accuracies.

On the other hand, in the surface acoustic wave apparatus 201 described in Japanese Unexamined Patent Application Publication No. H10-41776, the electrical connection between the terminal electrodes 204 and 205 on the base substrate 202 and the surface wave device 207 is made by the anisotropic conductive sheet 206. However, the surface acoustic wave apparatus 201 does not form a surface wave sensor apparatus. That is, the surface acoustic wave device 207 is only accommodated within an enclosed space surrounded by the base substrate 202, the frame 203, and the lid 209, and it is not intended to be used as the surface wave sensor apparatus and for detecting a detection substance contained in a liquid.

Also, in the surface acoustic wave apparatus 251, the apparatus is filled with the die-bond member 267 in a state of the metallic bumps 260 and 261 respectively being abutted by the through-hole conductors 263 and 264, so that the conjugation has been made by curing the die-bond member 267. Thus, since the die-bond member 267 is fluid before curing, it must be handled with care, so that there has been a problem of complicated bonding.

Also, in the surface acoustic wave apparatus 251, the surface acoustic wave device 259 is sealed in a region surrounded by the base substrate 252 and a cap member 271, and it is not intended to be used as a surface wave apparatus such as an in-liquid substance detection sensor.

As described above, the surface acoustic wave apparatuses described in Japanese Unexamined Patent Application Publication No. H10-41776 and Japanese Unexamined Patent Application Publication No. 2001-102905 disclose structural examples in that the surface acoustic wave device is electrically connected to electrodes on the base substrate. However, these surface acoustic wave apparatuses cannot be used for detecting a substance contained in a liquid.

SUMMARY OF THE INVENTION

In order to overcome the problems described above, preferred embodiments of the present invention provide a reliable surface wave sensor apparatus that is capable of easily detecting with high accuracy a substance contained in a liquid, even if it is provided in small quantities, as well as being capable of simplifying the manufacturing method and being difficult to be short circuited even when the liquid adheres to an electrical connection portion.

A surface wave sensor apparatus according to a preferred embodiment of the present invention includes a base substrate having first and second principal surfaces opposing each other; a first through-hole conductor arranged to penetrate the second principal surface of the base substrate from the first principal surface; a terminal electrode arranged on the second principal surface of the base substrate to be electrically connected to the first through-hole conductor; a thermo-compression anisotropic conductive sheet arranged on the first principal surface of the base substrate to be electrically connected to an end of the through-hole conductor; and a surface acoustic wave device bonded on the base substrate with the thermo-compression anisotropic conductive sheet, wherein the surface acoustic wave device includes a piezoelectric substrate having first and second principal surfaces opposing each other, at least one IDT disposed on the first principal surface of the piezoelectric substrate, an insulating protection film arranged to cover the IDT, and a second through-hole conductor electrically connected to the IDT and arranged to lead to the second principal surface of the piezoelectric substrate from the first principal surface, and wherein the first and second through-hole conductors overlap with each other via the thermo-compression anisotropic conductive sheet so that the second through-hole conductor is electrically connected to the first through-hole conductor of the base substrate with the thermo-compression anisotropic conductive sheet.

A surface wave sensor apparatus according to another preferred embodiment of the present invention includes a base substrate having first and second principal surfaces opposing each other; a terminal electrode arranged on the first principal surface of the base substrate; a thermo-compression anisotropic conductive sheet arranged on the first principal surface of the base substrate so as to be electrically connected to the terminal electrode; and a surface acoustic wave device bonded on the base substrate with the thermo-compression anisotropic conductive sheet, wherein the surface acoustic wave device includes a piezoelectric substrate having first and second principal surfaces opposing each other, at least one IDT disposed on the first principal surface of the piezoelectric substrate, an insulating protection film arranged to cover the IDT, and a through-hole conductor electrically connected to the IDT and arranged to lead to the second principal surface of the piezoelectric substrate from the first principal surface, and wherein the through-hole conductor overlaps with the terminal electrode via the thermo-compression anisotropic conductive sheet so that the through-hole conductor is electrically connected to the terminal electrode of the base substrate with the thermo-compression anisotropic conductive sheet.

The surface wave sensor apparatus may further include an insulating material member provided on the first principal surface of the base substrate so as to at least remove a region where the surface acoustic wave device is attached on the first principal surface of the base substrate.

The surface wave sensor apparatus may further include a detection film, wherein the surface acoustic wave device increases the mass of the detection film by the reaction with a specific substance so that the detection film applies a load corresponding to the increase in mass to the piezoelectric substrate.

The insulating protection film may also serve as the detection film. Alternatively, the detection film may be laminated on the insulating protection film.

A plurality of the surface acoustic wave devices may be mounted on one base substrate, and at least one surface acoustic wave device among the plurality of the surface acoustic wave devices may be provided with the detection film while at least one surface acoustic wave device among the remaining surface acoustic wave devices may be provided with no detection film.

A plurality of the surface wave devices may be mounted on one base substrate; each of the plurality of the surface wave devices may be provided with the detection film; and the detection film of at least one surface acoustic wave device may react with a substance different from those of the detection films of the other surface acoustic wave devices.

The detection film may react with a biochemical substance by biochemical reaction so as to increase its mass, thereby forming a biosensor.

When the surface wave sensor apparatus according to various preferred embodiments of the present invention is the biosensor, an antigen or an antibody may be fixed to the detection film; the biochemical substance may be the antigen or the antibody; and the biochemical reaction may be immune reaction.

In the surface wave sensor apparatus according to a preferred embodiment of the present invention, the second principal surface of the base substrate is provided with the terminal electrode, and the first through-hole conductor is provided to be electrically connected to the terminal electrode and to penetrate the second principal surface from the first principal surface. On the first principal surface of the base substrate, the surface acoustic wave device is bonded on the base substrate with the thermo-compression anisotropic conductive sheet. The first and second through-hole conductors overlap with each other via the thermo-compression anisotropic conductive sheet so that the second through-hole conductor, arranged to lead to the second principal surface of the piezoelectric substrate from the first principal surface, is electrically connected to the first through-hole conductor of the base substrate with the thermo-compression anisotropic conductive sheet.

Therefore, in the surface wave sensor apparatus according to a preferred embodiment of the present invention, the electrical connection can be made to the outside by the terminal electrode arranged on the second principal surface of the base substrate, i.e., on the principal surface opposite to that where the surface acoustic wave device is mounted. Moreover, in this surface acoustic wave device, at least one IDT is provided on the first principal surface of the piezoelectric substrate, which is the principal surface opposite to that where the thermo-compression anisotropic conductive sheet is laminated, and the insulating protection film is arranged to cover the IDT. As a result, even when a small amount of liquid adheres to the propagating region of surface acoustic waves on the piezoelectric substrate where the IDT is provided, the load of a substance in a liquid or the liquid itself can be detected by the change in load due to the adhesion of the liquid. Hence, using a small amount of liquid, a target detection substance in a liquid or the liquid can be detected. Furthermore, since the IDT is covered with the insulating protection film, a short circuit due to adhesion of the liquid to the IDT cannot occur. Moreover, since the electrical connection portion includes the second through-hole conductor provided in the piezoelectric substrate and the thermo-compression anisotropic conductive sheet, on the first principal surface of the piezoelectric substrate where liquid of the surface acoustic wave device is imparted, the electrical connection portion is difficult to expose to the outside, so that the short circuit is difficult to occur. Accordingly, upon detecting a target detection substance in a liquid or in the liquid, not only is the operation facilitated but also the measurement reliability can be improved.

In another preferred embodiment of the present invention, the surface acoustic wave device is bonded on the base substrate with the thermo-compression anisotropic conductive sheet therebetween; in surface acoustic wave device, the IDT is disposed on the first principal surface of the piezoelectric substrate opposite to that where the thermo-compression anisotropic conductive sheet is laminated; and the IDT is covered with the insulating protection film. Hence, in the surface wave sensor apparatus according to another preferred embodiment of the present invention, even when a small amount of liquid is imparted to the first principal surface of the piezoelectric substrate, a substance in a liquid or the liquid can be detected. More specifically, on the basis of the change in an exciting condition of surface acoustic waves due to the load change, a substance in liquid itself or the liquid can be detected.

Furthermore, since the IDT is covered with the insulating protection film as well as the electrical connection of the surface acoustic wave device to the outside is made on the side where the thermo-compression anisotropic conductive sheet is provided, the short circuit and the change in characteristics due to the adhesion of liquid are difficult to occur.

Hence, upon detecting a target detection substance in a liquid or the liquid, not only is the operation facilitated but also the measurement reliability can be improved.

In the surface wave sensor apparatus according to preferred embodiments of the present invention, when the insulating material member is provided on the first principal surface of the base substrate so as to at least remove a region where the surface acoustic wave device is attached on the first principal surface of the base substrate, the invasion of the liquid on the side of the second principal surface of the surface acoustic wave device can be suppressed by the insulating material member, so that the short circuit can be further securely prevented.

When the detection film is further provided, in which the surface acoustic wave device increases the mass of the detection film by the reaction with a specific substance so that the detection film applies a load corresponding to the increase in mass to the piezoelectric substrate, on the basis of the change in load due to the mass increase of the detection film, a specific substance in liquid can be easily detected with high accuracies.

When the protection film also serves as the detection film, the detection film need not be separately formed, so that the manufacturing process is facilitated and the surface wave sensor apparatus can be provided with a simplified structure.

However, the detection film may also be laminated on the protection film. In this case, the detection film may be made from wide variety of materials different from that of the protection film, and the detection film that is most suitable for the target detection substance can be easily formed.

When a plurality of the surface acoustic wave devices are mounted on one base substrate, and at least one surface acoustic wave device among the plurality of the surface acoustic wave devices is provided with the detection film while at least one surface acoustic wave device among the remaining surface acoustic wave devices is provided with no detection film, by comparing the output of the surface acoustic wave device having no detection film with that of the surface acoustic wave device having the detection film, the measurement accuracies can be improved.

When a plurality of the surface acoustic wave devices are mounted on one base substrate, each of the plurality of the surface acoustic wave devices is provided with the detection film, and the detection film of at least one surface acoustic wave device reacts with a substance different from those of the detection films of the other surface acoustic wave devices, two or more kinds of the target detection substance can be detected using the surface wave sensor apparatus according to preferred embodiments the present invention.

When the detection film reacts with a biochemical substance by biochemical reaction so as to increase its mass, thereby forming a biosensor, a target detection substance in blood or body fluid, for example, can be easily detected very accurately according to preferred embodiments of the present invention. Since the measurement portion including the IDT is especially covered with the insulating protection film, the measurement portion is difficult to be contaminated with blood or body fluid and the apparatus has a comparatively simplified structure in that the surface acoustic wave device is bonded on the base substrate with the thermo-compression anisotropic conductive sheet, a disposable and inexpensive biosensor can be provided according to preferred embodiments of the present invention.

When an antigen or an antibody is fixed to the detection film, the biochemical substance is the antigen or the antibody, and the biochemical reaction is an immune reaction, a reliable immune sensor apparatus capable of using a small amount of blood or body fluid as a test substance can be provided according to preferred embodiments of the present invention.

Other features, elements, steps, characteristics and advantages of the present invention will become more apparent

DETAILED DESCRIPTION OF THE PREFERRED EMBODIMENTS

The present invention will be disclosed below by describing specific preferred embodiments of the present invention with reference to the drawings.

Figure 1A:
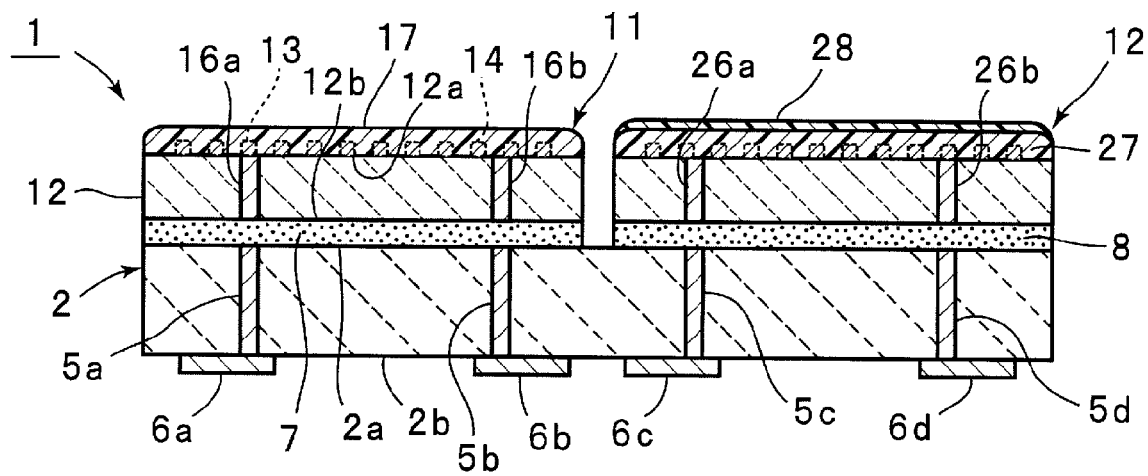
FIGS. 1(a) and 1(b) are a front sectional view of a surface wave sensor apparatus according to a first preferred embodiment of the present invention and a schematic plan view showing the electrical configuration of a surface acoustic wave device used in the surface wave sensor apparatus, respectively.
Figure 1B:
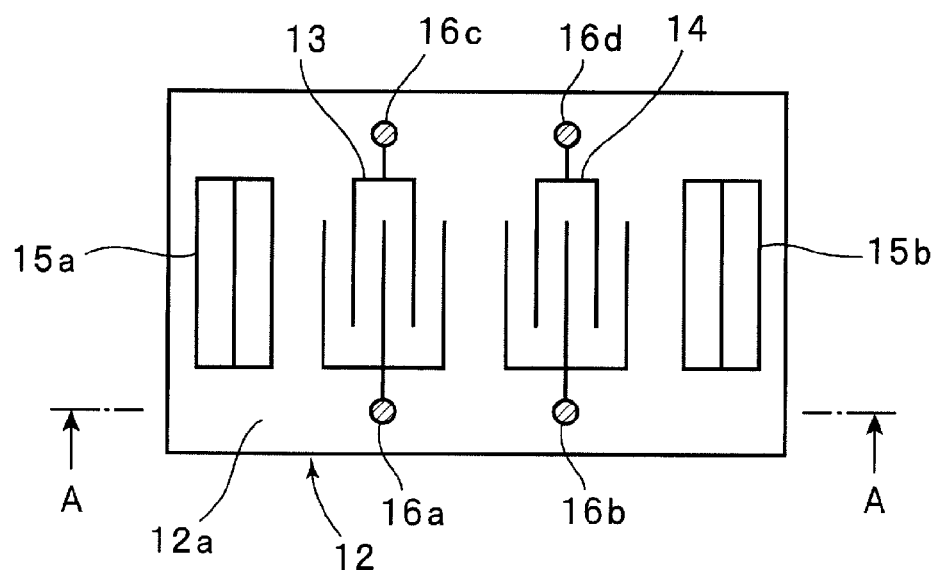

FIGS. 1(a) and 1(b) are a front sectional view of a surface wave sensor apparatus according to a first preferred embodiment of the present invention and a schematic plan view of a surface acoustic wave device used in the surface wave sensor apparatus, respectively.

A surface wave sensor apparatus 1 includes a base substrate 2. The base substrate 2 may be composed of appropriate insulating ceramics such as alumina. However, the base substrate 2 may also be made of another insulating material other than the ceramics.

The base substrate 2 includes a first principal surface 2a and a second principal surface 2b opposing the first principal surface 2a. On the insulating substrate 2, first and second surface acoustic wave devices 11 and 12 are mounted as a plurality of surface acoustic wave devices.

The surface acoustic wave device 11 includes a substantially rectangular plate-shaped piezoelectric substrate 12. The piezoelectric substrate 12 includes a first principal surface 12a and a second principal surface 12b opposing the first principal surface 12a. FIG. 1(b) is a schematic plan view showing the electrode configuration disposed on the piezoelectric substrate 12 of the surface acoustic wave device 11. On the first principal surface 12a of the piezoelectric substrate 12, a plurality of IDTs 13 and 14 are arranged. In the region where the IDTs 13 and 14 are provided, reflectors 15a and 15b are arranged on both sides of the surface acoustic wave propagating direction.

On the other hand, as shown in FIG. 1(a), in the piezoelectric substrate 12, through-hole conductors 16a and 16b are arranged so as to lead to the second principal surface 12b from the first principal surface 12a. The through-hole conductors 16a and 16b are electrically connected to first ends of the IDTs 13 and 14 shown in FIG. 1(b), respectively. FIG. 1(a) shows a section portion along the line A-A of FIG. 1(b). Thus, as shown in FIG. 1(b), second through-hole conductors 16c and 16d are further arranged so as to be connected to second ends of the IDTs 13 and 14, respectively.

The piezoelectric substrate 12 may be made of piezoelectric ceramics, such as lead zirconate titanate ceramics, or piezoelectric single crystal. Also, the piezoelectric substrate 12 may have a structure of a piezoelectric thin film disposed on an insulating substrate such as alumina, or a piezoelectric substrate.

The second through-hole conductors 16a to 16d may be made of an appropriate metal or alloy such as Ag and Cu. The forming of the through-hole conductors 16a to 16d may appropriately use a baking method in that after forming through-holes in the piezoelectric substrate 12, the holes are filled with conductive paste which is to be baked, or a solidifying method in that a liquid metal is pressed into the through-holes to be solidified.

The IDTs 13 and 14 and the reflectors 15a and 15b may be made of an appropriate metal or alloy such as Al and an Al alloy.

In the surface acoustic wave device 11, an insulating protection film 17 is arranged to cover the IDTs 13 and 14 and the reflectors 15a and 15b on the piezoelectric substrate 12. The insulating protection film 17 is provided for preventing a short circuit of the IDTs 13 and 14 due to a liquid sample. Hence, the insulating protection film 17 may be made of an appropriate insulating material. Preferably, it is made of a water-proof insulating material. Such a material for the insulating protection film 17 may include $SiO_2$, SiN, polyimide, AlN, and $Al_2O_3$.

First through-hole conductors 5a and 5b are arranged so as to lead to the second principal surface 2b from the first principal surface 2a on the base substrate 2. The through-hole conductors 5a and 5b may be made of an appropriate metal or alloy such as Ag and Al. The through-hole conductors 5a and 5b may be formed by a baking method in that after forming through-holes in the base substrate 2, the holes are filled with conductive paste which is to be baked. Alternatively, the through-hole conductors 5a and 5b may be formed by filling the through-holes with a liquid metal which is to be solidified or plated.

On the second principal surface 2b of the base substrate 2, terminal electrodes 6a and 6b are disposed and are preferably made of an appropriate metal or alloy such as Ag and Cu. The terminal electrodes 6a and 6b are electrically connected to ends of the first through-hole conductors 5a and 5b, respectively.

On the other hand, on the first principal surface 2a of the base substrate 2, a thermo-compression anisotropic conductive sheet 7 is provided. According to the present preferred embodiment, the surface acoustic wave device 11 is bonded and fixed on the first principal surface 2a of the base substrate 2 by the thermo-compression anisotropic conductive sheet 7 from the second principal surface 12b of the piezoelectric substrate 12. In this case, the thermo-compression anisotropic conductive sheet 7 is softened due to heat, and when members are bonded together, by interposing the thermo-compression anisotropic conductive sheet 7 between the members so as to be pressed, the thermo-compression anisotropic conductive sheet 7 functions to bond the members together. The thermo-compression anisotropic conductive sheet 7 is preferably made by dispersing conductive particles in a resin composition that is softened due to heat such that it exhibits a bonding force after it is cooled. At this time, the thermo-compression anisotropic conductive sheet 7 may also use a sheet made of a thermosetting material which is cured by heat. When the surface acoustic wave device 11 is pressed and bonded on the base substrate 2 with the thermo-compression anisotropic conductive sheet 7 therebetween, by its pressing force, the dispersed conductive particles cohere in the thickness direction to form a track extending in the thickness direction. On the other hand, the electrical connection is not generated in the surface direction of the thermo-compression anisotropic conductive sheet 7. Thus, as shown in FIGS. 1(a) and 1(b), when the first through-hole conductors 5a and 5b formed on the base substrate 2 and the second through-hole conductors 16a and 16b formed on the piezoelectric substrate 12 are arranged to overlap in the thickness direction with the thermo-compression anisotropic conductive sheet 7 therebetween, by pressing and bonding the surface acoustic wave device 11 on the base substrate 2 with the thermo-compression anisotropic conductive sheet 7 therebetween, the first through-hole conductors 5a and 5b and the second through-hole conductors 16a and 16b can be electrically connected together. In this electrical connection structure, since the track is not formed in the surface direction of the anisotropic conductive sheet 7, even when a water droplet adheres on the side the anisotropic conductive sheet 7, a short circuit cannot occur.

More specifically, water droplets cannot be electrically connected to the through-hole conductors 5a, 5b, 16a, and 16b.

The material of such a thermo-compression anisotropic conductive sheet 7 is not specifically limited; however it may include a resin composition, such as an epoxy resin, having Au particles dispersed therein.

As shown in FIG. 1(a), a second surface acoustic wave device 12, in the same way as in the first surface acoustic wave device 11, is also mounted on the base substrate 2. That is, the terminal electrodes 6c and 6d formed in the same way as in the terminal electrodes 6a and 6b are arranged below the surface acoustic wave device 12, and the first through-hole conductors 5c and 5d are provided as well so as to be electrically connected to the terminal electrodes 6c and 6d, respectively. The piezoelectric substrate of a surface acoustic wave device 21 is structured in the same way as in the surface acoustic wave device 11. Accordingly, a piezoelectric substrate 22 is provided with second through-hole conductors 26a and 26b that are electrically connected to the first through-hole conductors 5c and 5d with a thermo-compression anisotropic conductive sheet 8. The surface acoustic wave device 21 is configured in the same way as in the surface acoustic wave device 11 except for the second surface acoustic wave device 21 provided with a detection film 28 arranged to cover a insulating protection film 27.

The detection film 28 preferably has a structure of a synthetic resin film having an antigen or an antibody fixed thereto. Such a synthetic resin film may include a film made of an appropriate polymeric material capable of chemically bonding the antigen or the antibody.

Figure 2:
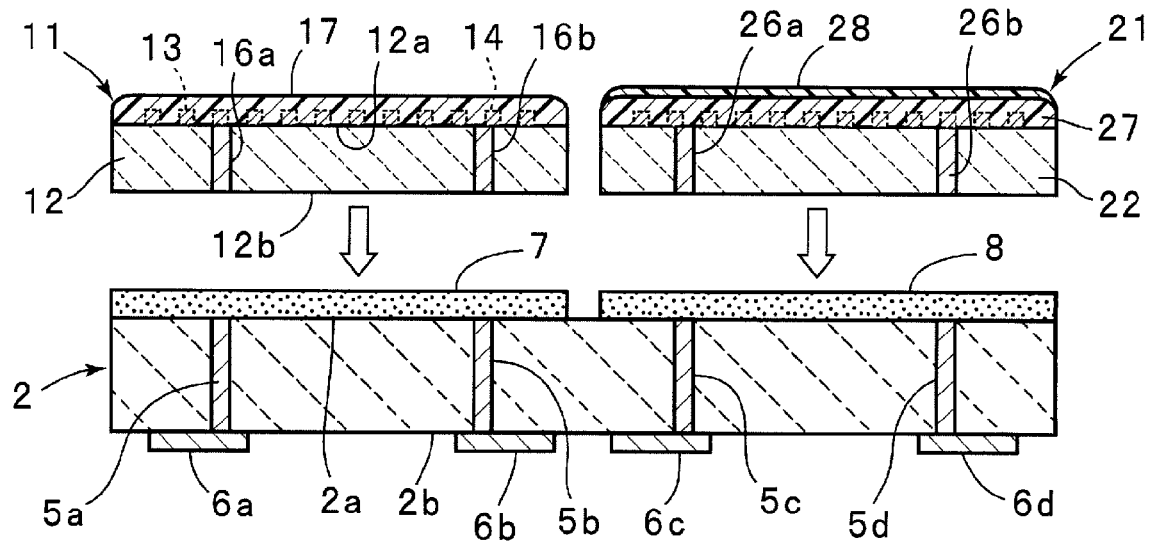
FIG. 2 is a front sectional view for illustrating the manufacturing process of the surface wave sensor apparatus shown in FIGS. 1(a) and 1(b).

When manufacturing the surface wave sensor apparatus 1, as shown in FIG. 2, the apparatus can be obtained by the steps of preparing the base substrate 2; arranging the thermo-compression anisotropic conductive sheets 7 and 8 on the base substrate 2; and pressing and bonding the surface acoustic wave devices 11 and 21 onto the base substrate 2 via the thermo-compression anisotropic conductive sheets 7 and 8, respectively, while heating them. Alternatively, the thermo-compression anisotropic conductive sheets 7 and 8 are bonded on the surface acoustic wave devices 11 and 21, respectively, in advance, and then, the base substrate 2 may be bonded on the surface acoustic wave devices 11 and 12 via the thermo-compression anisotropic conductive sheets 7 and 8.

Figure 3:
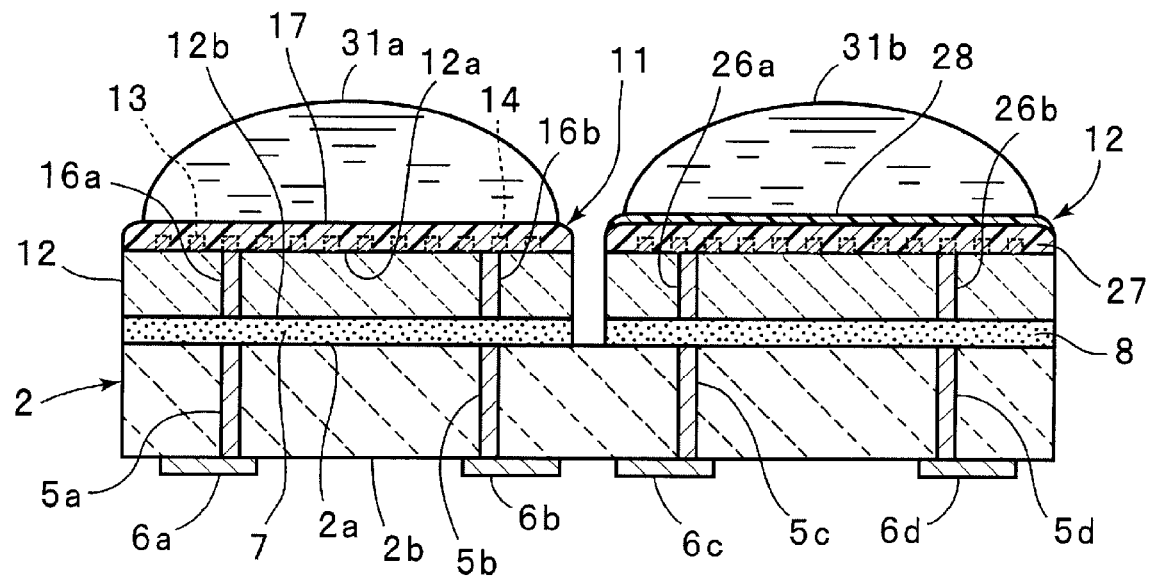
FIG. 3 is a front sectional view for showing an example of the measuring process using the surface wave sensor apparatus shown in FIGS. 1(a) and 1(b).

A process for detecting a substance in a liquid sample using the surface wave sensor apparatus 1 will be described. First, as shown in FIG. 3, entire liquids 31a and 31b are stuck on the first and second surface acoustic wave devices 11 and 21 of the surface wave sensor apparatus 1. When the liquids 31a and 31b are stuck, they may be applied on the surface acoustic wave devices 11 and 12 by correcting the liquids with a pipette or a syringe, for example. In any method, the detection may be made by sticking the liquid with comparatively small quantity, such as about 1 µL to about 1 mL. In this case, the antigen or the antibody, which is a target measuring object, is contained in the liquids 31a and 31b. Specifically, the test substance including an antigen or an antibody to be coupled to the antigen or the antibody fixed on the detection film 28 by immune reaction is supplied as the liquids 31a and 31b.

In the surface acoustic wave device 21, since the antigen or the antibody is fixed on the detection film 28, an antigen or an antibody in the liquid 31b is coupled to the antigen or the antibody by the immune reaction so as to form an immune composite. That is, the antigen or the antibody in the liquid 31b is coupled to the detection film 28.

On the other hand, in the surface acoustic wave device 11, since the detection film is not provided, the antigen or the antibody in the liquid 31a cannot be coupled by the immune reaction.

Thus, in the surface acoustic wave device 1, when the liquids 31a and 31b then are removed from the state shown in FIG. 3, since in the surface acoustic wave device 21, the antigen or the antibody in the liquid 31b is coupled to the detection film 28 by the immune reaction, the mass of the detection film 28 increases. Whereas, in the surface acoustic wave device 11, the load applied to the piezoelectric substrate 12 does not change.

Hence, by the difference between the output due to the change in load applied to the piezoelectric substrate 22 on the side of the surface acoustic wave device 21 and the output on the side of the surface acoustic wave device 11, the presence of the antigen or the antibody coupled to the detection film can be detected.

Furthermore, when a calibration curve is prepared in advance using a standard liquid sample including the antigen or the antibody with a known density, the amount of the antigen or the antibody existing in the liquid 31b, i.e., the density of the antigen or the antibody in the liquid 31b, can also be determined in quantity.

In addition, in the surface wave sensor apparatus 1, in a portion having the liquids 31a and 31b imparted thereto, i.e., on the first principal surfaces 12a and 22a of the piezoelectric substrates 12 and 22, the electrodes, such as the IDTs 13 and 14, are covered with the insulating protection films 17 and 27, respectively. Hence, the liquids 31a and 31b cannot come in direct contact with the electrodes.

Moreover, the electrical connection portion between the IDTs 13 and 14 and the terminal electrodes 6a to 6d for electrically connection to the outside includes the through-hole conductors 5a to 5d, 16a, 16b, 26a, and 26b provided inside the base substrate 2 and the piezoelectric substrates 12 and 22 and the thermo-compression anisotropic conductive sheets 7 and 8. The through-hole conductors 5a to 5d, 16a, 16b, 26a, and 26b herein are embedded within the base substrate 2 and the piezoelectric substrates 12 and 22, so that it is difficult for them to be in direct contact with the liquids. Also, the thermo-compression anisotropic conductive sheets 7 and 8 have electrical insulative properties in their surface direction as mentioned above. Hence, even when the liquids 31a and 31b are stuck on the side of the thermo-compression anisotropic conductive sheet 7 in between the base substrate 2 and the piezoelectric substrate 12, the liquids cannot be conducted to the through-hole conductor 5a.

Thus, according to the present preferred embodiment, it is difficult to generate measurement failure and changes in measured value due to an undesired short circuit while using liquid samples, and furthermore, it is difficult to have deterioration with age in measurement accuracies.

Therefore, the presence detection and the determination in quantity of a detection substance in liquid can be performed with high accuracies, thus, increasing measurement reliability to a large extent.

As described above, the apparatus can be obtained by pressing and bonding the surface acoustic wave devices 11 and 21 onto the base substrate 2 via the thermo-compression anisotropic conductive sheets 7 and 8, respectively, so that the simplification of the manufacturing process and the reduction in number of components can be achieved, leading to the miniaturization of the surface wave sensor apparatus 1 and the reduction in cost thereof. Thus, in the medical field, the surface wave sensor apparatus 1 may be preferably used as a biosensor including blood or body fluid as a detection sample. Since the surface wave sensor apparatus 1 is inexpensive, a disposable sensor can be easily provided.

According to the present preferred embodiment, a plurality of the surface acoustic wave devices 11 and 21 are respectively combined with the thermo-compression anisotropic conductive sheets 7 and 8 so as to respectively correspond thereto. Alternatively, a plurality of thermal surface acoustic wave devices may be bonded on one sheet of the base substrate 2 via large one sheet of the thermo-compression anisotropic conductive sheet. That is, the thermo-compression anisotropic conductive sheets 7 and 8 may also be integrated.

Figure 4:
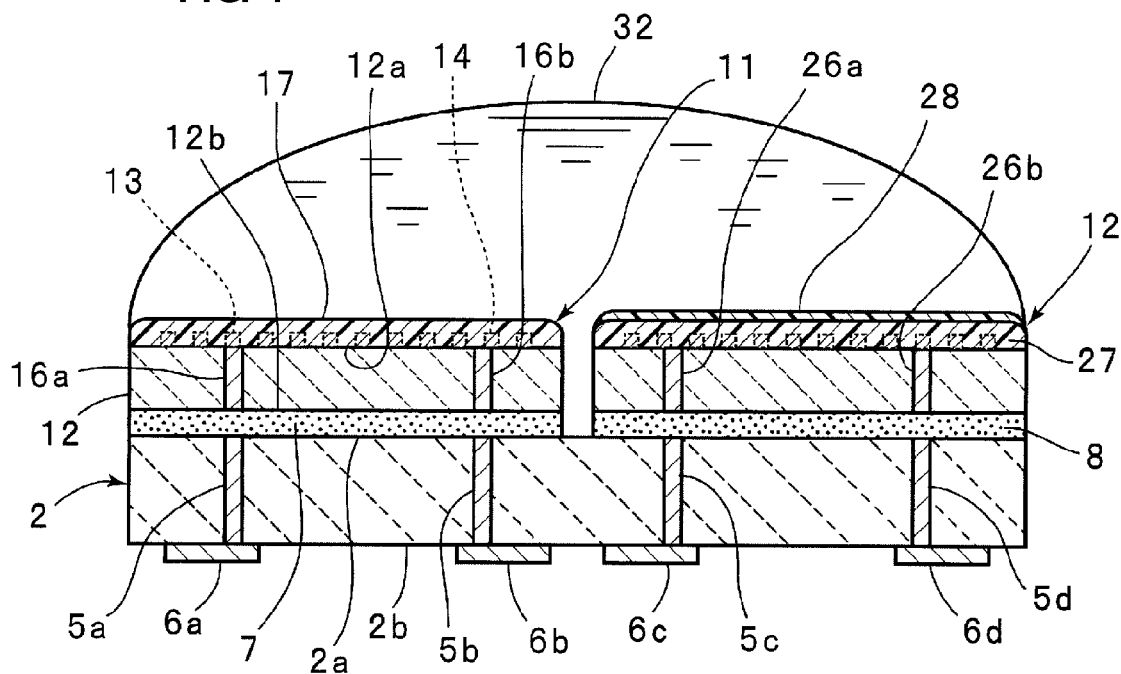
FIG. 4 is a front sectional view for showing another example of the measuring process using the surface wave sensor apparatus shown in FIGS. 1(a) and 1(b).

Also, in the measuring method described above, on the first and second surface acoustic wave devices 11 and 21, the liquids 31a and 31b are stuck, respectively, with a pipette, etc. Alternatively, as shown in FIG. 4, a large liquid droplet 32 may also be stuck to cover the upper surfaces of the first and second surface acoustic wave devices 11 and 21 for measurement.

Figure 5:
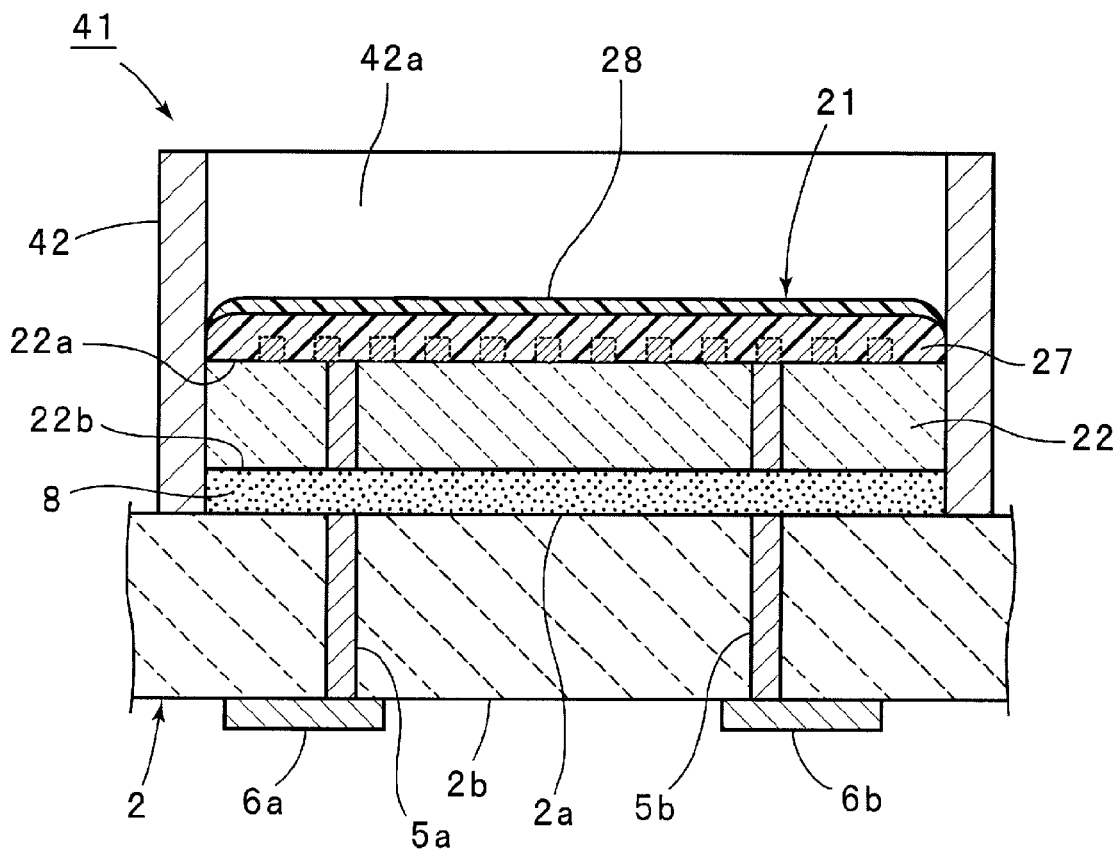
FIG. 5 is a front partially cutaway sectional view for illustrating a modification of the surface wave sensor apparatus according to the preferred embodiment shown in FIGS. 1(a) and 1(b).

Furthermore, FIG. 5 is a front partially cutaway sectional view for illustrating an enlarged essential part of a modification of the surface wave sensor apparatus 1 according to the present preferred embodiment. FIG. 5 showing the modified surface wave sensor apparatus 41 illustrates a portion corresponding to the portion of the second surface acoustic wave device 21 of the surface wave sensor apparatus 1 shown in FIGS. 1(*a*) and 1(*b*). More specifically, the second surface acoustic wave device 21 is mounted on the base substrate 2 in the same way as in the preferred embodiment described above. The difference is that a frame 42 having an opening 42a upwardly opened so as to surround the surface acoustic wave device 21 is fixed to the first principal surface 2a of the base substrate 2. The frame 42 may be made of an appropriate insulating material. By forming a space surrounded by the frame 42, the lateral leakage of liquid can be prevented when the liquid is supplied onto the detection film 28 of the surface acoustic wave device 21. That is, by preventing the liquid leakage outside the frame 42, the liquid can be prevented from coming around into the second principal surface 2b of the base substrate 2.

Hence, preferably, the frame 42 is fixed in a fluid sealed manner to the first principal surface 2a of the base substrate 2. As shown in FIG. 5, more preferably, the frame 42 is arranged so as to contact in a fluid sealed manner with the sides of the piezoelectric substrate 22 of the second surface acoustic wave device 21 and the thermo-compression anisotropic conductive sheet 8, thereby preventing the liquid from leaking below the surface acoustic wave device 21.

FIG. 5 shows only the side of the second surface acoustic wave device 21. However, it is preferable to similarly provide the frame also on the side of the first surface acoustic wave device 11.

In FIG. 5, the frame 42 preferably made of an insulating material is arranged around the surface acoustic wave device. However, the present invention is not limited to the frame, and it is preferable that an insulating member be provided on the first principal surface so as to at least remove the region where the surface acoustic wave device is attached on the first principal surface. Such an insulating member may also include an insulating film other than the frame 42. By any structure, the liquid leakage outside the region where the surface acoustic wave device is attached can be prevented by the insulating portion, preventing the undesired short circuit.

Figure 6:
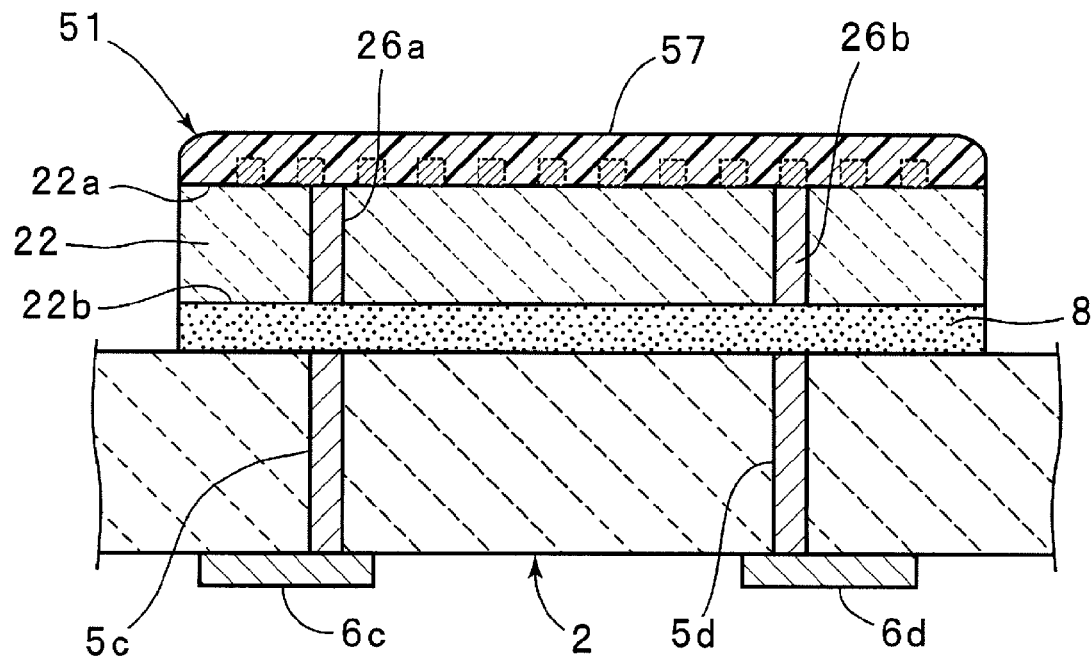
FIG. 6 is a front partially cutaway sectional view for illustrating another modification of the surface wave sensor apparatus according to the preferred embodiment shown in FIGS. 1(a) and 1(b).

FIG. 6 is a front partially cutaway sectional view for illustrating another modification of the surface wave sensor apparatus according to the present preferred embodiment. In the surface wave sensor apparatus 1, the detection film 28 is preferably used for the second surface acoustic wave device 21; alternatively, like a second surface acoustic wave device 51 shown in FIG. 6, an insulating protection film 57 may also serve as a detection film. More specifically, the insulating protection film 57 herein is preferably composed of a synthetic resin film having the antigen or the antibody fixed thereon to be coupled to an antigen or an antibody contained in a liquid sample. According to a preferred embodiment of the present invention, in such a manner, the detection film is not necessarily provided separately from the insulating protection film. In this case, the configuration of the surface acoustic wave device can be further simplified.

Figure 7:
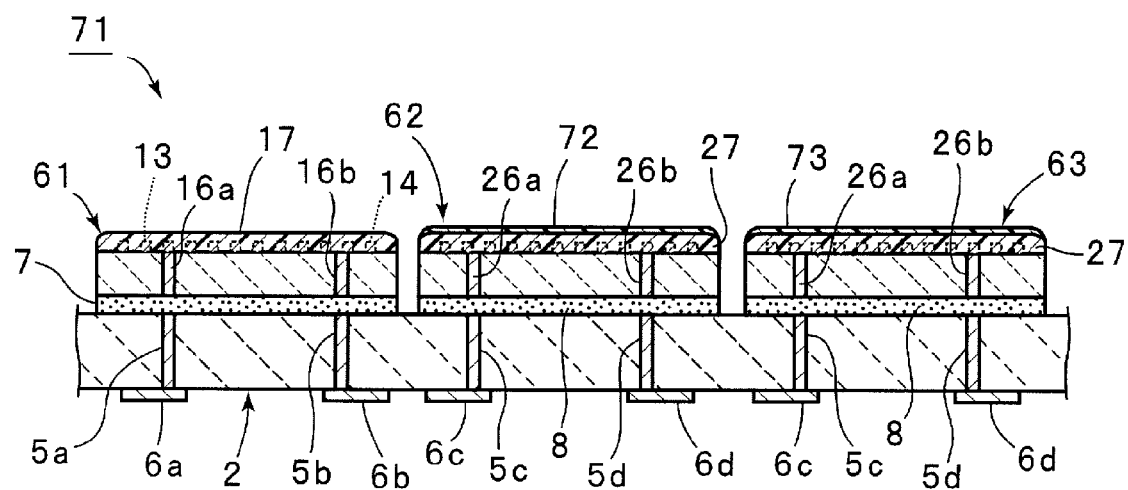
FIG. 7 is a surface sectional view for illustrating still another modification of the surface wave sensor apparatus shown in FIGS. 1(a) and 1(b).

According to the first preferred embodiment, preferably a plurality of thermal surface acoustic wave devices 11 and 21 are arranged on one sheet of the base substrate 2, and one surface acoustic wave device 11 of the plurality of thermal surface acoustic wave devices 11 and 21 is not provided with the detection film while the other surface acoustic wave device 21 being provided with the detection film. However, as shown in FIG. 7, three or more surface acoustic wave devices 61 to 63 may be mounted on one sheet of the base substrate 2. A surface wave sensor apparatus 71 may be configured so that in surface acoustic wave devices 62 and 63 having detection films 72 and 73 respectively formed thereon, the detection films 72 and 73 react with detection substances different from each other, respectively. In this case, a plurality of kinds of the detection substance contained in liquid can be measured by the surface wave sensor apparatus 71.

According to the preferred embodiment shown in FIGS. 1(*a*) and 1(*b*), the detection film 28 preferably has a structure in which an antigen or an antibody is fixed on the synthetic resin film. Alternatively, the detection film may also connect a detection substance contained in liquid thereto using a biochemistry reaction other than the immune reaction.

Furthermore, the application in which a detection substance contained in a liquid sample is coupled to the detection film by a chemical reaction other than the biochemistry reaction so as to increase the mass of the detection film may also incorporate preferred embodiments of the present invention. In this case, the detection film 28 may connect or include a chemical substance reacting with the chemical substance in the liquid sample.

Also, according to a preferred embodiment of the present invention, the detection film is not necessarily essential, so that the apparatus may also be configured to only detect the presence of the stuck liquid. Specifically, only the first surface acoustic wave device 11 shown in FIGS. 1(a) AND 1(b) may also be mounted on the base substrate 2. In this case, by the change in load due to the presence of the stuck liquid on the first surface acoustic wave device 11, the presence of the stuck liquid can be detected. That is, the surface wave sensor apparatus according to a preferred embodiment of the present invention may also be used as a liquid detection sensor.

A surface wave sensor apparatus may also be configured such that, on the base substrate 2, only the second surface acoustic wave device 21 shown in FIGS. 1(a) and 1(b) is mounted. In this case, a calibration curve is prepared in advance with a standard liquid sample with a known density using a plurality of surface wave sensor apparatuses, and when determining the quantity of a practical liquid sample, the measurement may be made using the surface wave sensor apparatus 1 having only one surface acoustic wave device 21 mounted so as to obtain the density of the detection substance in the liquid from the calibration curve. Hence, in the surface wave sensor apparatus according to a preferred embodiment of the present invention, only one surface acoustic wave device may be mounted on the base substrate.

Figure 8:
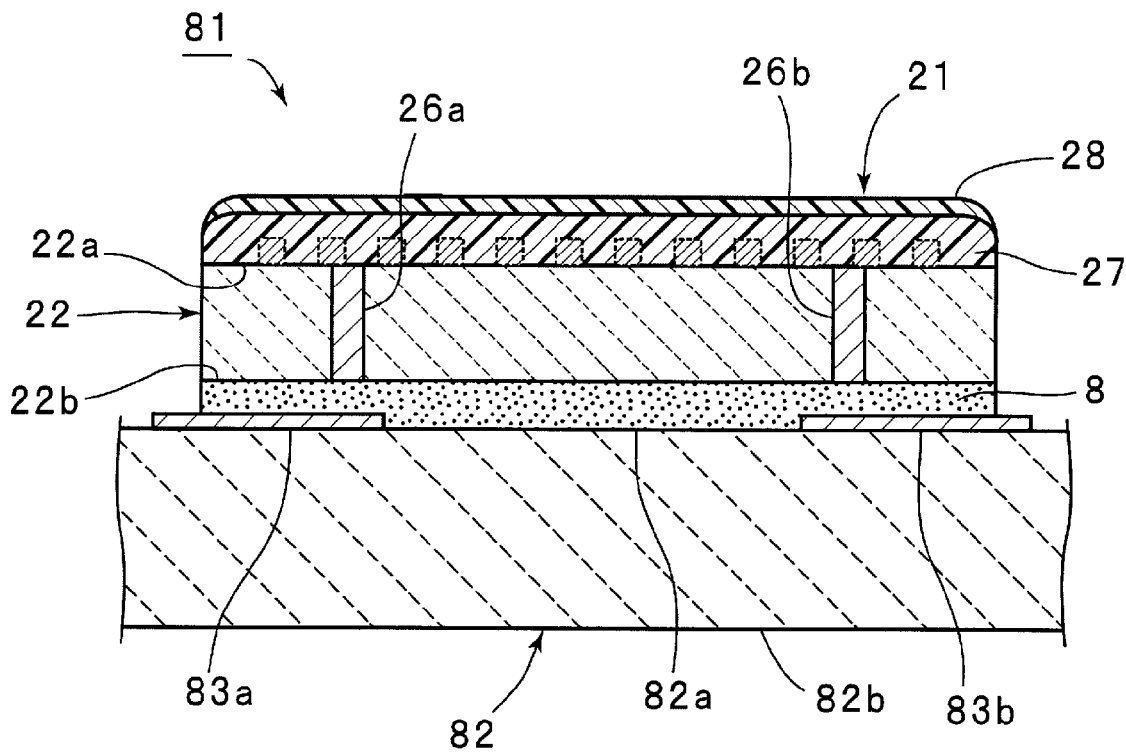
FIG. 8 is a front sectional view of a surface wave sensor apparatus according to a second preferred embodiment of the present invention.
Figure 9:
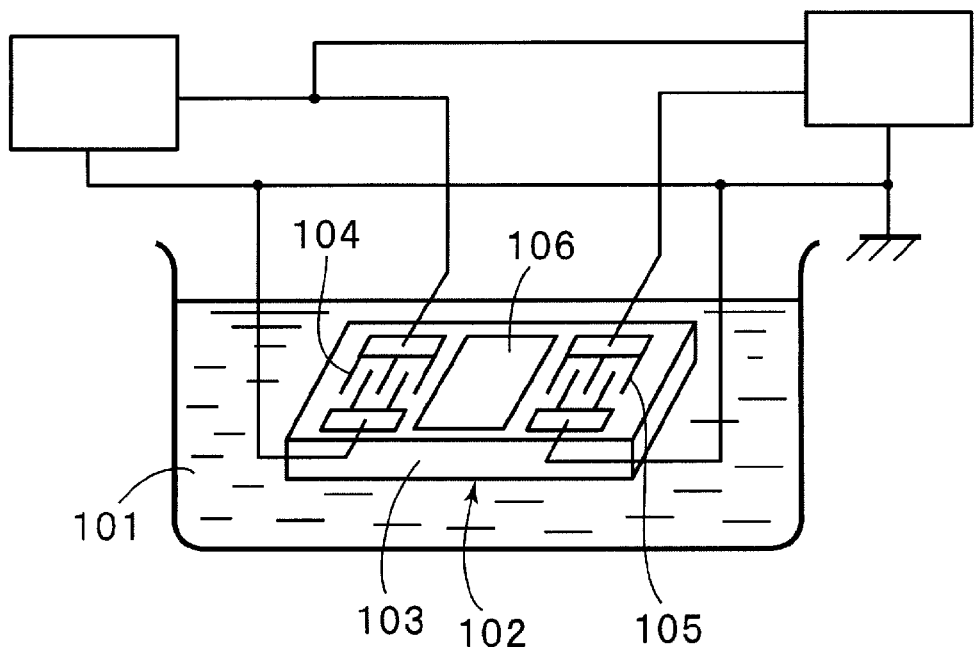
FIG. 9 is a schematic structural view for illustrating a conventional in-liquid substance detection sensor.
Figure 10:
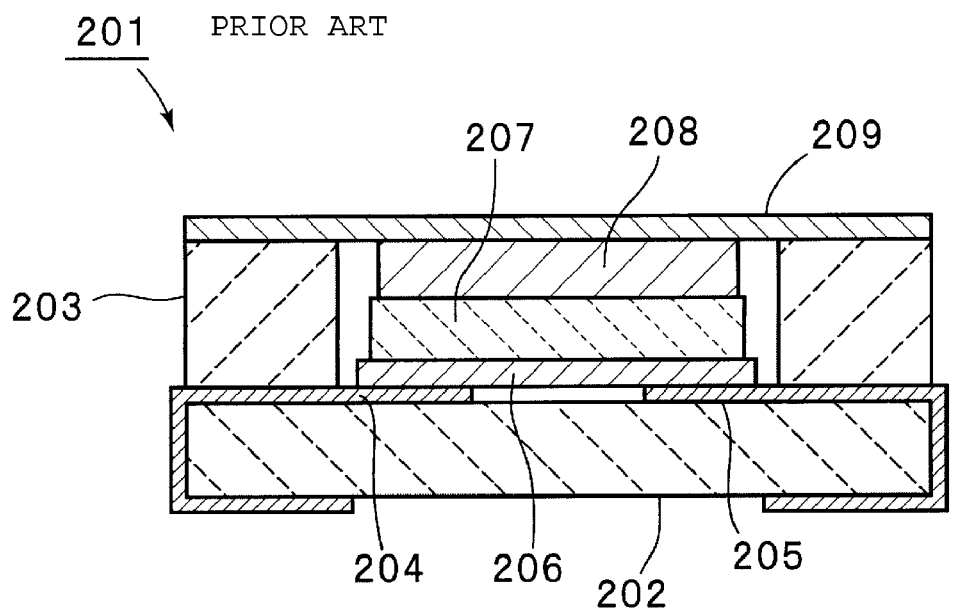
FIG. 10 is a front sectional view showing an example of a conventional surface acoustic wave apparatus.
Figure 11:
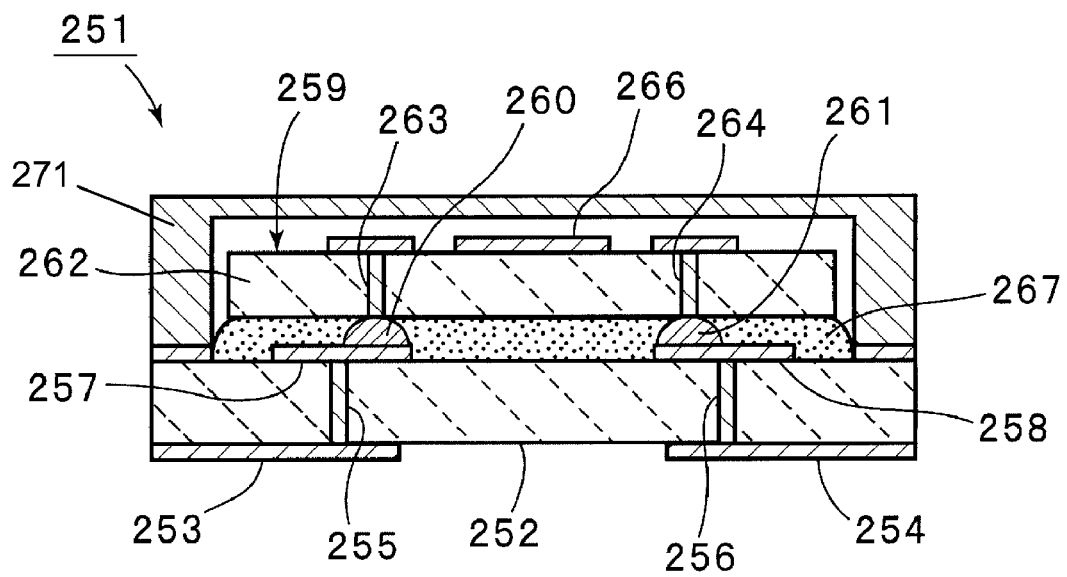
FIG. 11 is a front sectional view showing another example of the conventional surface acoustic wave apparatus.

FIG. 8 is a schematic front sectional view of a surface wave sensor apparatus according to a second preferred embodiment of the present invention.

A surface wave sensor apparatus 81 includes a base substrate 82. The base substrate 82 is not provided with a first through-hole conductor. The base substrate 82 includes a first principal surface 82a and a second principal surface 82b opposing the first principal surface 82a. On the first principal surface 82a, first and second surface acoustic wave devices are mounted in the same way as in the preferred embodiment shown in FIGS. 1(a) and 1(b). However, in FIG. 8, only the portion where the second surface acoustic wave device 21 is arranged is illustrated.

Also, on the first principal surface 82a of the base substrate 82, terminal electrodes 83a and 83b are provided. On the terminal electrodes 83a and 83b, through-hole conductors 26a and 26b of the second surface acoustic wave device 21 are electrically connected together with the thermo-compression anisotropic conductive sheet 8. In other words, the terminal electrodes 83a and 83b are arranged at a position overlapping with the through-hole conductors 26a and 26b via the thermo-compression anisotropic conductive sheet 8. The terminal electrodes 83a and 83b extend outside the region where the thermo-compression anisotropic conductive sheet 8 is provided, enabling the electrical connection to the outside.

Also, according to the present preferred embodiment, a liquid as a test substance is imparted from the side of the first principal surface 22a where the IDTs of the second surface acoustic wave device 21 are provided, and the terminal electrodes 83a and 83b for electrical connection to other portions of the surface acoustic wave device 21 are arranged on the side of the second principal surface 22b of the piezoelectric substrate 12. Furthermore, since the electrical connection portion, other than the portion where the terminal electrodes 83a and 83b are provided, is not exposed, the undesired short circuit due to the adhesion of the liquid can be prevented.

However, according to the second preferred embodiment, since the terminal electrodes 83a and 83b are upwardly exposed, it is preferable that the electrical connection portion be derived on the side of the second principal surface 2b of the base substrate 2 by the through-hole conductors 5a to 5f like in the first preferred embodiment.

In the surface wave sensor apparatus 81, although not shown in FIG. 8, the first surface acoustic wave device 11 is preferably mounted on the base substrate 82 in the same way as in the second surface acoustic wave device 21.

While preferred embodiments of the present invention have been described above, it is to be understood that variations and modifications will be apparent to those skilled in the art without departing the scope and spirit of the present invention. The scope of the present invention, therefore, is to be determined solely by the following claims.

What is claimed is:

1. A surface wave sensor apparatus, comprising:
a base substrate having first and second principal surfaces opposing each other;
a first through-hole conductor arranged to penetrate the second principal surface of the base substrate from the first principal surface;
a terminal electrode arranged on the second principal surface of the base substrate so as to be electrically connected to the first through-hole conductor;
a thermo-compression anisotropic conductive sheet arranged on the first principal surface of the base substrate so as to be electrically connected to an end of the through-hole conductor; and
a surface acoustic wave device bonded on the base substrate with the thermo-compression anisotropic conductive sheet; wherein
the surface acoustic wave device includes a piezoelectric substrate having first and second principal surfaces opposing each other, at least one IDT disposed on the first principal surface of the piezoelectric substrate, an insulating protection film arranged to cover the IDT, and a second through-hole conductor electrically connected to the IDT and arranged to extend to the second principal surface of the piezoelectric substrate from the first principal surface;
the first and second through-hole conductors overlap with each other via the thermo-compression anisotropic conductive sheet so that the second through-hole conductor is electrically connected to the first through-hole conductor of the base substrate with the thermo-compression anisotropic conductive sheet;
the thermo-compression anisotropic conductive sheet includes conductive particles dispersed in a resin composition, the resin composition being made of a material that is softened when heated and has a bonding force when cooled;
the dispersed conductive particles cohere to each other in a thickness direction of the thermo-compression anisotropic conductive sheet to provide a conductive track extending in the thickness direction of the thermo-compression anisotropic conductive sheet and arranged to provide an electrical connection between the first and second through-hole conductors;
a detection film is disposed on the insulating protection film; and a mass of the detection film is increased by a reaction of the detection film with a specific substance so that the detection film applies a load corresponding to the increased mass to the piezoelectric substrate.

2. The surface wave sensor apparatus according to claim 1, further comprising an insulating material member arranged on the first principal surface of the base substrate so as to at least remove a region where the surface acoustic wave device is attached on the first principal surface of the base substrate.

3. The surface wave sensor apparatus according to claim 1, wherein the insulating protection film also defines the detection film.

4. The surface wave sensor apparatus according to claim 1, wherein the detection film is laminated on the insulating protection film.

5. The surface wave sensor apparatus according to claim 1, wherein a plurality of the surface acoustic wave devices are mounted on one base substrate, and at least one surface acoustic wave device among the plurality of the surface acoustic wave devices is provided with the detection film while at least one surface acoustic wave device among the remaining surface acoustic wave devices is provided with no detection film.

6. The surface wave sensor apparatus according to claim 1, wherein a plurality of the surface acoustic wave devices are mounted on one base substrate, each of the plurality of the surface acoustic wave devices is provided with the detection film, and the detection film of at least one surface acoustic wave device reacts with a substance different from those of the detection films of the other surface acoustic wave devices.

7. The surface wave sensor apparatus according to claim 1, wherein the detection film reacts with a biochemical substance by biochemical reaction so as to increase its mass, thereby defining a biosensor.

8. The surface wave sensor apparatus according to claim 7, wherein an antigen or an antibody is fixed to the detection film, the biochemical substance is the antigen or the antibody, and the biochemical reaction is an immune reaction.

9. A surface wave sensor apparatus, comprising:
a base substrate having first and second principal surfaces opposing each other;
a terminal electrode arranged on the first principal surface of the base substrate;
a thermo-compression anisotropic conductive sheet arranged on the first principal surface of the base substrate to be electrically connected to the terminal electrode; and
a surface acoustic wave device bonded on the base substrate with the thermo-compression anisotropic conductive sheet; wherein
the surface acoustic wave device includes a piezoelectric substrate having first and second principal surfaces opposing each other, at least one IDT disposed on the first principal surface of the piezoelectric substrate, an insulating protection film arranged to cover the IDT, and a through-hole conductor electrically connected to the IDT and arranged to extend to the second principal surface of the piezoelectric substrate from the first principal surface;
the through-hole conductor overlaps with the terminal electrode via the thermo-compression anisotropic conductive sheet so that the through-hole conductor is electrically connected to the terminal electrode of the base substrate with the thermo-compression anisotropic conductive sheet;
the thermo-compression anisotropic conductive sheet includes conductive particles dispersed in a resin composition, the resin composition being made of a material that is softened when heated and has a bonding force when cooled;
the dispersed conductive particles cohere to each other in a thickness direction of the thermo-compression anisotropic conductive sheet to provide a conductive track extending in the thickness direction of the thermo-compression anisotropic conductive sheet and arranged to provide an electrical connection between the through-hole conductor to the terminal electrode;
a detection film is disposed on the insulating protection film; and
a mass of the detection film is increased by a reaction of the detection film with a specific substance so that the detection film applies a load corresponding to the increased mass to the piezoelectric substrate.

10. The surface wave sensor apparatus according to claim 9, further comprising an insulating material member arranged on the first principal surface of the base substrate so as to at least remove a region where the surface acoustic wave device is attached on the first principal surface of the base substrate.

11. The surface wave sensor apparatus according to claim 9, wherein the insulating protection film also defines the detection film.

12. The surface wave sensor apparatus according to claim 9, wherein the detection film is laminated on the insulating protection film.

13. The surface wave sensor apparatus according to claim 9, wherein a plurality of the surface acoustic wave devices are mounted on one base substrate, and at least one surface acoustic wave device among the plurality of the surface acoustic wave devices is provided with the detection film while at least one surface acoustic wave device among the remaining surface acoustic wave devices is provided with no detection film.

14. The surface wave sensor apparatus according to claim 9, wherein a plurality of the surface acoustic wave devices are mounted on one base substrate, each of the plurality of the surface acoustic wave devices is provided with the detection film, and the detection film of at least one surface acoustic wave device reacts with a substance different from those of the detection films of the other surface acoustic wave devices.

15. The surface wave sensor apparatus according to claim 9, wherein the detection film reacts with a biochemical substance by biochemical reaction so as to increase its mass, thereby defining a biosensor.

16. The surface wave sensor apparatus according to claim 15, wherein an antigen or an antibody is fixed to the detection film, the biochemical substance is the antigen or the antibody, and the biochemical reaction is an immune reaction.

17. The surface wave sensor apparatus according to claim 1, wherein the electrical connection between the first and second through-hole conductors does not extend outside of the conductive track in a surface direction of the thermo-compression anisotropic conductive sheet that is substantially perpendicular to the thickness direction of the thermo-compression anisotropic conductive sheet.

18. The surface wave sensor apparatus according to claim 9, wherein the electrical connection between the through-hole conductor and the terminal electrode does not extend outside of the conductive track in a surface direction of the thermo-compression anisotropic conductive sheet that is substantially perpendicular to the thickness direction of the thermo-compression anisotropic conductive sheet.

* * * * *